United States Patent [19]

Korth

[11] Patent Number: 4,516,855

[45] Date of Patent: May 14, 1985

[54] METHOD AND APPARATUS FOR DETERMINING THE POLARIZATION STATE OF A LIGHT WAVE FIELD

[75] Inventor: Hans E. Korth, Stuttgart, Fed. Rep. of Germany

[73] Assignee: International Business Machines Corporation, Armonk, N.Y.

[21] Appl. No.: 359,406

[22] Filed: Mar. 18, 1982

[30] Foreign Application Priority Data

Apr. 4, 1981 [EP] European Pat. Off. ........ 81102533.5

[51] Int. Cl.³ .............................................. G01J 4/04
[52] U.S. Cl. .................................. 356/367; 356/369; 358/82; 358/107
[58] Field of Search ............... 356/347, 348, 351, 359, 356/360, 364, 366, 367, 369; 350/369; 250/225; 358/81, 82, 107

[56] References Cited

U.S. PATENT DOCUMENTS 3,631,254 12/1971 Covault ........................... 250/225 X
3,864,513 2/1975 Halajian et al. .
4,085,421 4/1978 Gilmour ................................ 358/81

Primary Examiner—Davis L. Willis
Assistant Examiner—Matthew W. Koren
Attorney, Agent, or Firm—T. Rao Coca

[57] ABSTRACT

The local state of polarization of a light wave field is determined by measuring the radiation transmitted by one or several polarizers with three different azimuth angles. A modified TV camera is used having its usually provided tri-color filters replaced by polarization filters whose azimuth angles differ from each other by 60° respectively. On a connected color monitor, the local polarization state can be concluded from the local brightness, the hue, and the saturation. The polarization camera can preferably be used for ellipsometric measurings, in an interferometric system for surface topography, and in interferometric holography. The display of the polarization state of the color monitor can be supplemented by electronic means, e.g. emphasizing points having the same state of polarization.

7 Claims, 7 Drawing Figures

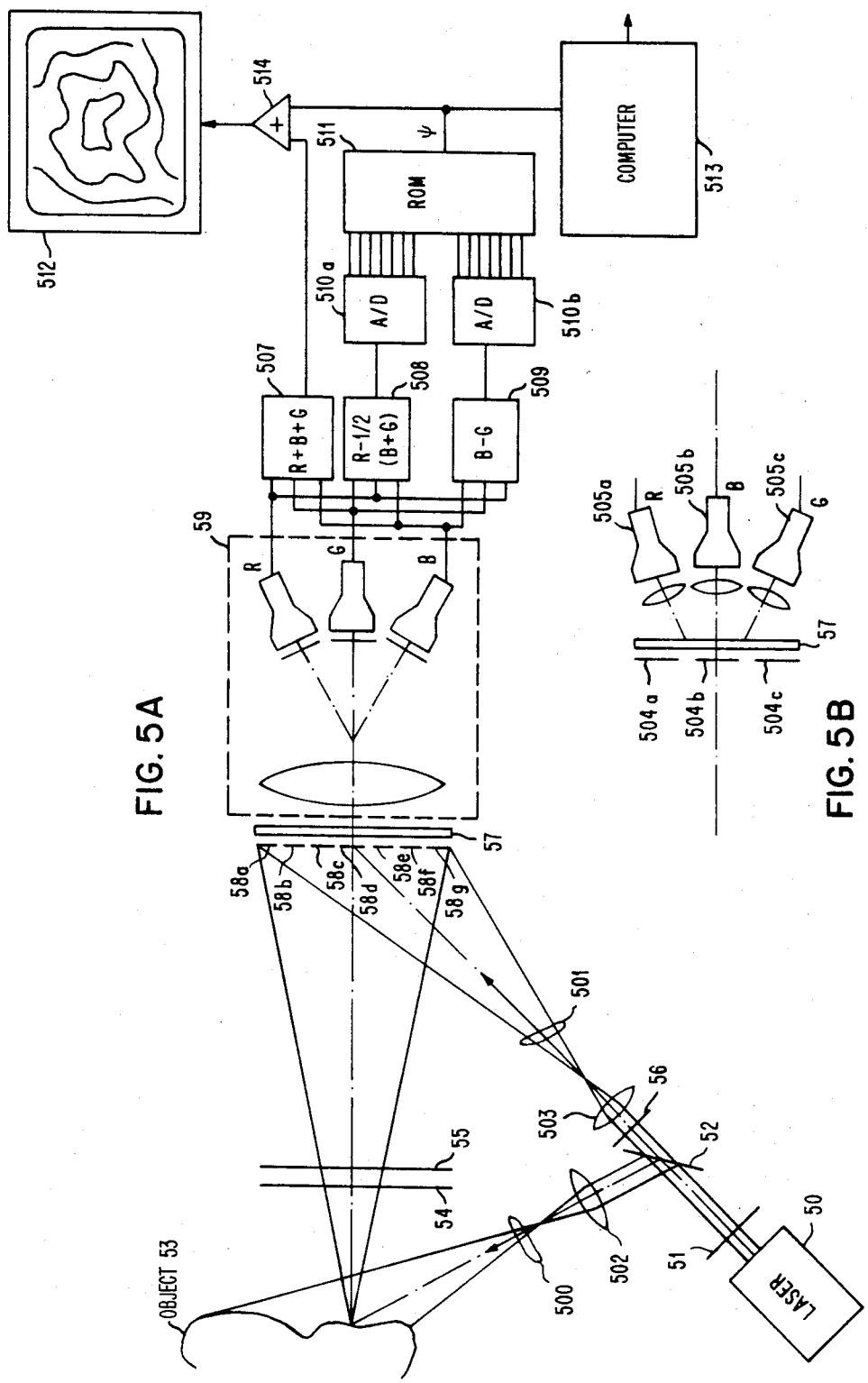

METHOD AND APPARATUS FOR DETERMINING THE POLARIZATION STATE OF A LIGHT WAVE FIELD

FIELD OF THE INVENTION

The invention generally relates to a method for determining the polarization state of a light wave field, and to an apparatus for carrying out the method. More particularly, the invention relates to the application of the above method and apparatus for interferometric and holographic measurings.

BACKGROUND OF THE INVENTION

Determining the local state of polarization of a generally elliptically polarized light wave field demands for each point a time-consuming measuring of the intensity transmitted by an analyzer at various azimuth angles. Evaluating the measuring results to determine the so-called polarization ellipse defining the state of polarization at the respective point of the wave field is also complicated and in many cases only possible with a computer. A point-by-point examination of large light wave fields with polarized radiation is therefore exceptionally complex; on the other hand, for many measurings it is very useful to know this state of polarization.

One such case is the problem of determining the local characteristics of thin transparent layers over a substrate, e.g. insulation and passivation layers in the production of integrated circuits. To obtain the necessary circuit parameters the thickness of these layers is to be determined with great precision during or after their production. If the index of refraction of the layer is known, this can principally be effected with interferometric measuring methods. However, the indices of refraction of thin layers depend very much on their method of production so that their precision definition is impossible without actually measuring. For simultaneously determining layer thickness and index of refraction of a thin transparent layer, the ellipsometric method offers maximum precision. In this method, a polarized light beam of small diameter and oblique incidence is directed onto the layer to be examined, and the intensity of the reflected beam is determined as a function of the azimuth angle of an analyzer. The measured intensity distribution determines the state of polarization of the reflected beam in the form of a so-called polarization ellipse which in turn permits determination of thickness and index of refraction of the layer.

Such a point-by-point measuring technique requires a relatively large amount of time. This is true also for those cases where measuring is effected in so-called automatic ellipsometers where the analyzer rotates with a high speed. For time reasons, the point-by-point ellipsometric measuring of large surfaces is therefore possible in exceptional cases only. Furthermore, the spatial resolution of the measuring is low owing to the oblique incidence.

Light wave fields with locally different polarization state can also be employed for a number of further applications, provided a speedy and local evaluation of the state of polarization is possible. Examples are photo-elasticity, crystal optics, or saccharimetry.

SUMMARY OF THE INVENTION

The present invention is intended to advance the teachings of the above indicated state of the art and has for its principle object a method for comprehensively evaluating a polarization field in a significantly reduced time.

Another object of the invention is to provide a method by means of which all points of a large light wave field can be measured in parallel to determine their polarization states.

A further object of the invention is to provide for improved ellipsometric or interferometric measuring methods applying the method for evaluating a polarization field.

Still another object of the invention is to provide an uncomplicated apparatus for carrying out the improved method of the invention.

The method for determining the polarization state of a light wave field, according to the invention, provides that for each point of the wave field the intensity transmitted by one or several polarizers is measured for three different transmission directions, each differing from the other by 60° respectively.

For carrying out the method of evaluating a polarization field, the invention suggests a modified colour TV camera (polarization camera) having the dichroic tricolour filters replaced by polarization filters whose transmission directions differ by 60° each. The output signal generated by this polarization camera contains all data on the state of polarization of the impinging radiation. If this output signal is directed onto a colour monitor, the distribution of brightness, hue, and saturation can be an indicator for the polarization state of the impinging radiation.

As it permits a quick visual display of a large polarization field, the polarization camera has a wide field of application. In an ellipsometric measuring device, the polarization camera can be used for continuously controlling a production line since visual observation presents an immediately comprehensive image to untrained operators. A visual comparison between the polarization image and a standard image of the examined surface easily reveals connections between the visible structure of a thin layer and its characteristics determined by the polarization image. Besides, the polarization image can be easily processed electronically or digitally to facilitate evaluation still further.

The thus offered elegant means for evaluating the polarization state represents a considerable improvement regarding the range of precision of known optical methods. The invention offers particularly advantageous application, e.g. in the field of interferometric surface topography, and of interferometric holography.

For making the polarization camera, the conventional types of known colour TV cameras can readily be referred to.

These and other objects and advantages of the present invention will become more apparent from the following detailed description taken in conjunction with the accompanying drawings.

BRIEF DESCRIPTION OF THE DRAWINGS

FIG. 5A shows application of the basic structure of FIG. 1 in a device for holographic interferometry with a polarization camera.

FIG. 5B shows an alternative part embodiment for the holographic interference arrangement of FIG. 5A.

DETAILED DESCRIPTION OF THE INVENTION

Structure and operation of the polarization camera will now be described with reference to an ellipsometric device.

Figure 1:
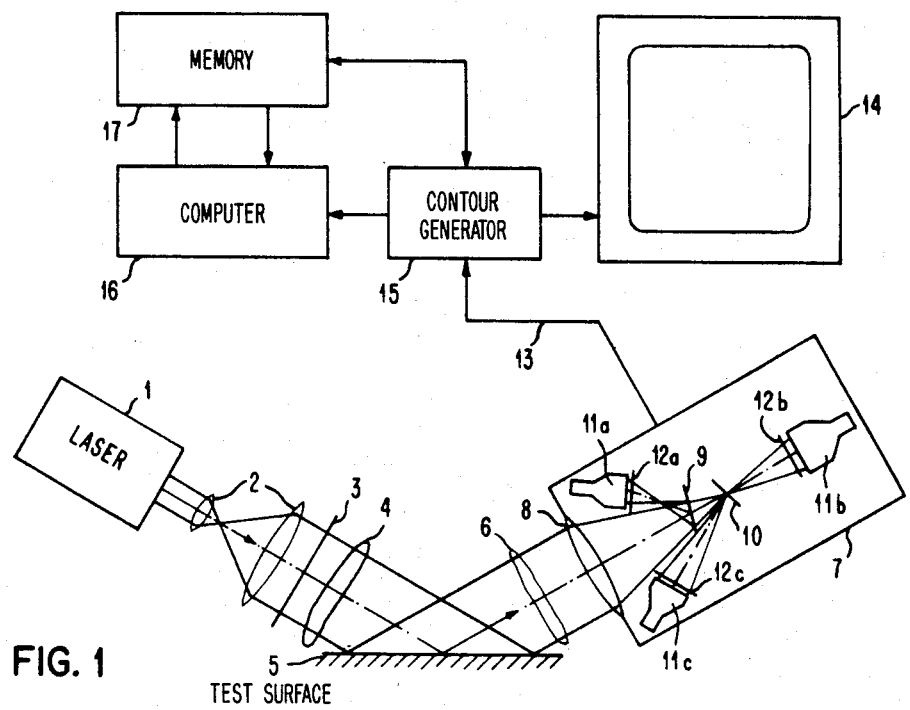
FIG. 1 is a schematic structure of the invention showing an ellipsometric measuring device with a polarization camera, with three pick-up tubes, a display and necessary interconnecting circuitry.

In FIG. 1, an ellipsometric measuring device consists of a conventional laser 1, followed by beam expansion optics 2 consisting of two collector lenses from which exits a beam 4 of enlarged diameter. The beam passes through polarizer 3 which is oriented at an azimuth angle of 45°, and reaches test surface 5 coated with a thin layer at an oblique angle of incidence. Upon reflection from surface 5, the linear polarization of beam 4 is disturbed so that there is a generally elliptic polarization in exit beam 6. Exit beam 6 reaches a polarization camera 7 comprising imaging optics 8, two beam splitters 9 and 10, and a total of three image converter tubes 11a, 11b, 11c each preceded by polarizers 12a, 12b, 12c whose transmission directions differ by 60° each. Orientation and degree of transmission of beam splitters 9 and 10 are selected in such a manner that each one of tubes 11 receives the same intensity. The output signal of polarization camera 7 reaches a colour TV monitor 14 via line 13. Further devices can be connected to line 13, if required, e.g. a contour generator 15 for generating lines of equal intensity or phase, as well as a computer 16 or a memory 17 for digital processing, or storing of the polarization image generated by polarization camera 7.

Polarization camera 7 is a commercially available colour TV camera containing polarizers (e.g. polarization foils) instead of the tricolour filters (green, red, blue).

Figure 2:
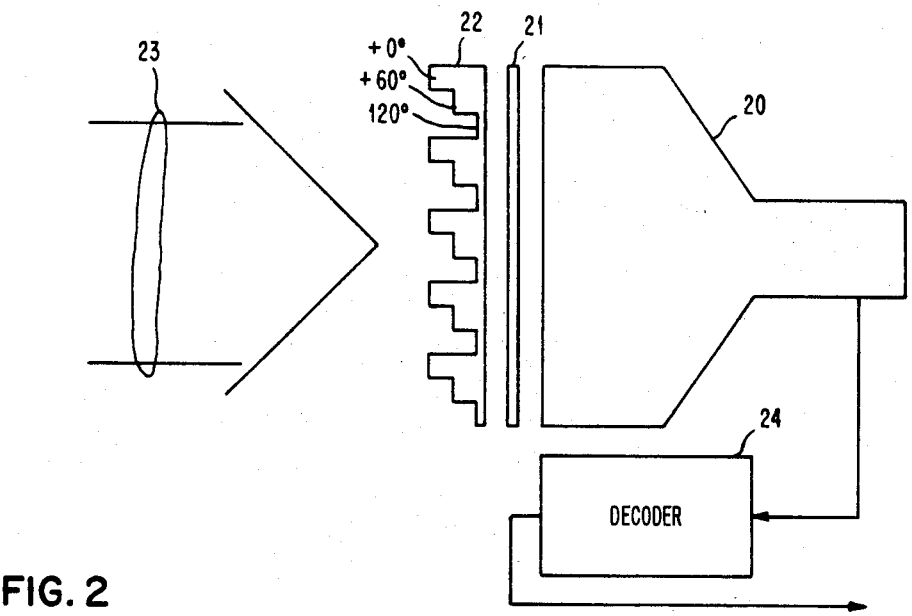
FIG. 2 shows an embodiment of a polarization camera with one pick-up tube.

FIG. 2 shows another embodiment of a polarization camera with one single image converter tube 20; it also corresponds to a known type of a colour TV tube where the tricolour filters are arranged stripe-wise, before the image converter tube. In the polarization camera, there is provided before the light admission surface of image converter tube 20 a polarization filter 21 and a stripe-shaped arrangement 22 of zones where the polarization direction of the impinging light beam 23 is turned by 0°, 60°, or 120°, respectively. This effect can e.g. be achieved through varying thicknesses of a polarization-rotating substance in layer 22. The sequential scanning of the image phase in tube 20 by the electron beam thus produces successively three signals corresponding to the areas of differing rotation of polarization; in a decoder 24, these signals can be separated electronically and will then correspond to the output signals of the three image converter tubes according to FIG. 1.

Figure 3A:
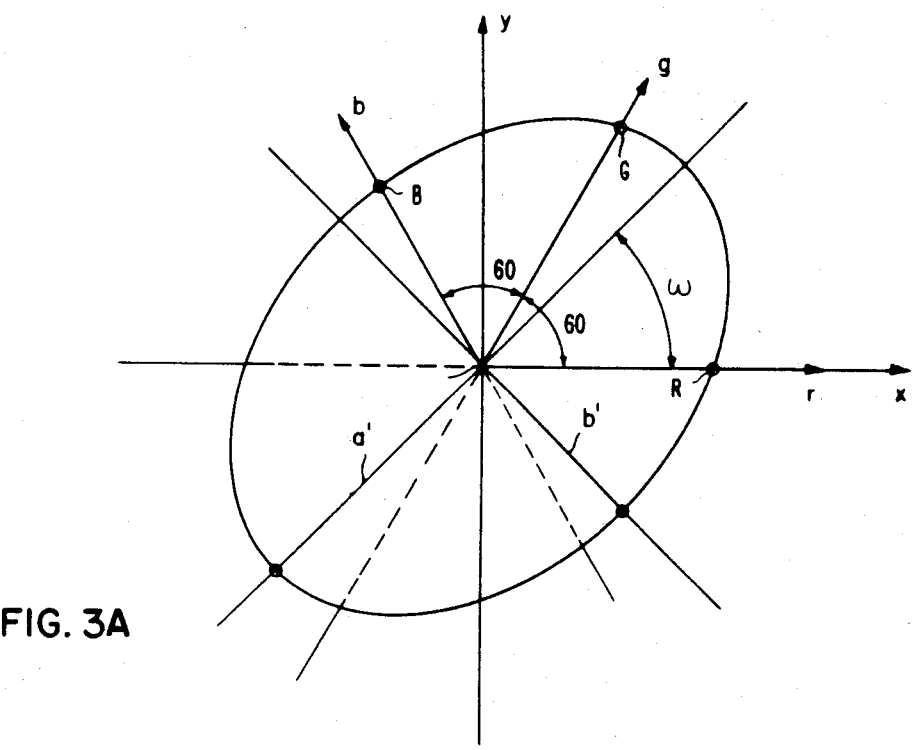
FIG. 3A is a diagram with a polarization ellipse to represent the signal processing in the polarization camera.

The operation of the polarization camera will now be specified with reference to the polarization ellipse represented in FIG. 3A. For an observer looking in the direction of the light reflected from surface 5 in FIG. 1, the tip of the electric vector of the light wave moves at each point of the respective light wave field through an ellipse, the so-called polarization ellipse. This ellipse is obtained through the composition of two linear oscillations polarized orthogonally to each other which show a mutual phase difference. The axis ratio a'/b' of the ellipse, and the position of the main axis in space (angle ω) is determined by the amplitude ratio, and the phase difference of the two linear oscillations. In FIG. 3A, the ellipse is recorded in a rectangular xy-coordinate system, where it is assumed that the x-direction coincides with the plane of incidence of the beam reflected from surface 5.

For each point of the beam reflected from surface 5 the individual local polarization ellipse has to be defined. This is achieved by means of the also recorded transmission directions marked r, g, b of the three polarizers in the polarization camera. Transmission direction r has been assumed to coincide with the plane of incidence. The directions r and g as well as g and b each include angles of 60°.

Points of intersection R, G, B of transmission directions r, g, b with the polarisation ellipse determine the size of the electric vector which for a predetermined position of the polarization ellipse is transmitted by each one of the three polarizers. The intensities recorded behind the analyzers by the image converter tubes correspond to the square of this value. With the thus measured values for R, G and B both the position (angle ω) and the form (axis ratio a'/b') of the polarization ellipse at the respective point of beam 6 are clearly defined. Since values R, B, G are generated by the polarization camera upon the scanning of beam 6 for each point of the wave field, the state of polarization of the entire wave fields impinging on the camera is determined after one scanning of this wave field, and can be displayed on a connected monitor. A particular correlation between position and shape of the polarization ellipse, and the parameters (i.e., brightness, hue, saturation) of the colour TV monitor relevant for visual display can be effected at discretion.

A particularly advantageous correlation of the measured polarization parameters with the parameters of a colour monitor can be found when certain analogies are observed between the polarization-optical measuring and the processing of colour signals in conventional colour TV systems. It is a known fact that in colour television two signals are used to transmit the information content of a colour image:

1. The so-called luminance signal which corresponds to the brightness of a point in the colour image and which in accordance with the following rule is composed of the three output signals of the image tubes for the colours R (for red), B (for blue), and G (for green):

$$Y = 0.3R + 0.59G + 0.11B$$

2. The chrominance signal whose phase position determines the hue, and whose amplitude determines the degree of saturation. This chrominance signal is produced through the amplitude modulation of an auxiliary colour carrier with two signals which are formed of linear combinations of R, B and G, and which for the so-called quadrature amplitude modulation are phase-shifted by 90° relative to each other. In the PAL colour TV system these signals are:

$$U = 0.493(B-Y)$$

$$V = 0.877(R-Y)$$

In the NTSC-system the following applies:

$$I = 0.6R - 0.028G - 0.32B$$

$$Q = 0.21R - 0.53G + 0.31B$$

Figure 3B:
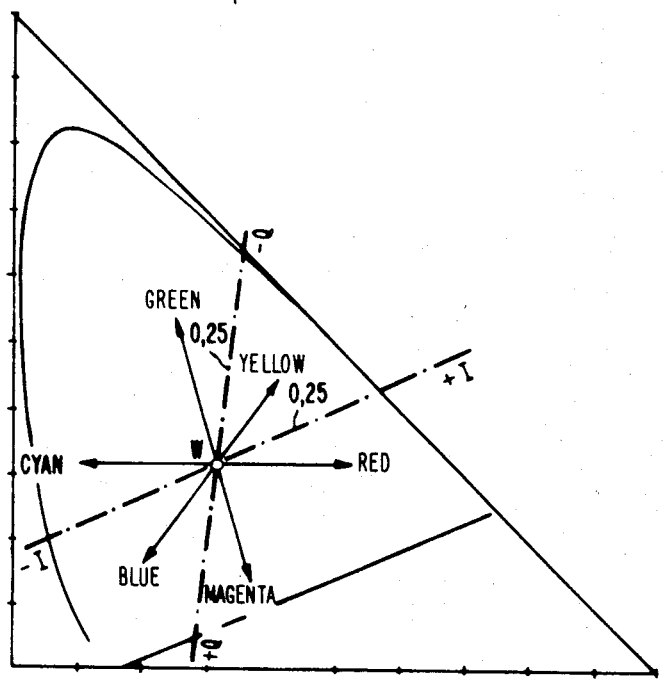
FIG. 3B shows a colour triangle known from the colour matrix field.

FIG. 3B shows the colour plane (colour triangle) known from colour matrix, through whose achromatic point W axes I and Q of an oblique angle coordinate system can be drawn which correspond to the above-mentioned signals I and Q. The U and V axes are slightly turned against the I and Q axis. Details of the colour TV techniques referred to here are state of the art and can be found, for example, in the following publications:
- W. A. Holm, Farbfernsehtechnik ohne Mathematik, Eindhoven, 1966.
- O. Limann, Fernsehtechnik ohne Ballast, Munchen, 1979.
- W. Dillenburger, Einfuhrung in die Fernsehtechnik, Berlin, 1969.
- B. Morgenstern, Farbfernsehtechnik 1977.

If the output signals of the polarization camera, at different positions of the polarizer, are also assumed to be tricolour signals R, G, B, and if with these signals the same combinations as in colour television are effected the following relations are obtained:
- the phase position of the polarization-optical "chrominance signal", or the hue, respectively corresponds to the position of the main axis of the polarization ellipse;
- the eccentricity (the axis ratio a'/b') of the polarization ellipse corresponds to the ratio of the amplitude of the polarization optical "chrominance signal" (or saturation) to the polarization optical "luminance" (or brightness).

To explain this connection, some borderline cases will be discussed:
(a) in circularly polarized light, all three image converter tubes of the polarization camera receive the same signal (R=B=G=1); in the colour triangle, this case corresponds to the achromatic point, since maximum luminance (Y=1) and absent chrominance (I=Q=0) coincide;
(b) in polarized light whose polarization direction coincides with one of the three transmission directions (e.g. r), the associated image converter tube receives a maximum signal (e.g. R=1), and the two other tubes, in accordance with the relation $I \sim \cos 2\phi$ receive the intensity I=0.25. The luminance thus decreases to the value 0.48, the chrominance increases (I=0.45, Q=0.16). This position of the polarization ellipse displays on the TV monitor an image point in the red spectral range with deep saturation. A rotation of the polarization plane of this linearly polarized light corresponds to a rotation of the associated vector in the colour triangle.

With increasing ellipticity of the light, the saturation decreases, and luminance increases.

The above discussed correlation of polarization-optical characteristics to characteristics of the chrominance signal results in a very advantageous means for the quantitative analysis of the polarization state through electronic evaluation of the chrominance signal for each point of the field of view. Since determining the relative phase in an electronic signal, and measuring the respective amplitude can be done very precisely, there is a high measuring resolution for the polarization-optical parameters.

To facilitate visual evaluation, the display on the colour monitor can be processed with electronic means (generator 15) in such a manner that there appear only points of the same brightness and/or the same hue, and/or the same saturation. This produces lines which resemble contour lines. The selection of the thus characterized point can be done very simply with electronic comparator circuits for the amplitudes, and/or the phases of the luminance and chrominance signals.

Figure 4:
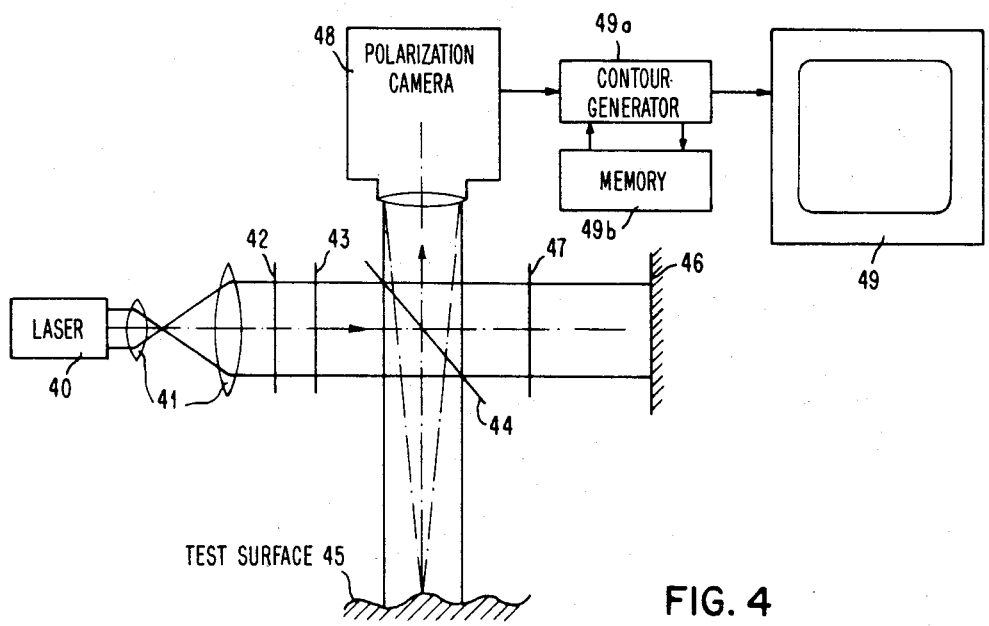
FIG. 4 shows application of the basic structure of FIG. 1 in an interferometric system for examining surfaces with a polarization camera.

FIG. 4 represents the use of the polarization camera in an interferometric device for examining surface topographies. A light source 40, preferably a laser, illuminates via beam expansion optics 41, a polarizer 42, a λ/4 plate 43, and a semi-transparent mirror 44 the surface 45 of an object to be examined, as well as a planar reference surface 46. Between beam splitter 44 and reference surface 46, a second λ/4 plate 47 is provided. The beams reflected from surfaces 45 and 46 reach a polarization camera 48 whose output signals are applied to a colour monitor 49. Electronic device 49a for producing contour lines, and storage 49b to store a reference pattern can selectively be provided between polarization camera 48 and colour monitor 49.

This surface topography device is based on the superposition of two circularly polarized wave fields with different rotation direction of the polarization vector. In this superposition, linearly polarized light is produced whose direction of polarization depends on the relative phase position of the two wave fields. In the arrangement according to FIG. 4, λ/4 plate 43 produces the circularly polarized light which is directed onto test surface 45, and which is reflected therefrom. The light which passes from the light source through beam splitter 44, and which is also circularly polarized is again converted upon the second passage through second λ/4 plate 47 into circularly polarized light which however with respect to the light reflected from surface 45 shows the reverse rotation direction. After the combining of the two reflected beam parts by beam splitter 44, a linearly polarized light wave field is obtained as input variation for polarization camera 48, the local polarization direction being determined by the phase shifts caused by irregularities on surface 45 at the various points of the reflected wave fields.

With the polarization camera, the "natural" interference fringes resulting from the FIG. 4 arrangement (corresponding to a difference of the polarization direction of 90°) can be supplemented by "artificial interference colours" which are between the natural interference fringes and which permit a quantitative interpolation. The resolution of this interpolation is very high; at a wave length of the light used of λ=633 nm, a rotation of the polarization by 180° corresponds for instance to a height difference of 158 nm. If the phase of the chrominance signals can be determined with electronic means with a precision of 1%, the measuring precision of the arrangement is better than 2 nm.

Memory 49b can be used for storing the surface profile of a reference surface, so that in the investigation of a surface with electronic means the difference between test surface and reference surface can be defined. The results of the comparison can then be superimposed on the test image on the monitor as a correction pattern.

FIG. 5 shows a use of the polarization camera for phase-true evaluation in holographic interferometry. In holographic interferometry, two holograms of an object to be examined for deformations are recorded on a record carrier, the first hologram corresponding to the non-deformed body, and the second corresponding to the deformed body. In the reconstruction of the double hologram, interferences are generated which supply information about the local deformations. Instead of a dual exposure, it is also possible to use the interference between the illuminated object itself and its holographic reconstruction. In hitherto known holographic interferometry, the sign of the deformation however can only be determined indirectly.

For clearly determining the sign of a deformation it is suggested in FIG. 5 to impress specific phase differences (0°, 60°, 120°) upon individual zones of the generated hologram recording to be able to determine in the reconstruction of the hologram the phase at each point of the reconstruction from the various known phase differences.

In the recording of the holograms, the light wave phase is encoded as polarization direction; the quantitative determination of the phase in the interference image of the reconstruction is then effected by means of a polarization camera.

With reference to FIG. 5A in the first step of the holographic interferometry, the hologram of an object 53 is to be produced on a holographic record carrier 57. For that purpose, light of a laser 50 is directed via a polarizer 51 and a beam splitter 52 as an object beam onto object 53, from which it is reflected and impinges via λ/4 plate 55 onto record carrier 57. If object 53 acts in a depolarizing manner—which is generally the case—a further polarizer 54 arranged before λ/4 plate 55 is required.

The light beam passing through beam splitter 52 passes as reference beam 501 a λ/4 plate 56 before impinging on record carrier 57. In the beam path of object beam and reference beam, imaging elements 502, 503 are provided in suitable locations.

λ/4 plates 55, 56 are oriented in such a manner that they product circularly polarized light with opposite rotation directions. The superposition of these two circularized waves on record surface 57 produces linearly polarized light whose polarization direction depends on the relative phase difference of the two circular waves.

Recording surface 57 is preceded by stripe-shaped polarizers 58a, 58b, ... whose directions of transmission differ by 60° respectively. Consequently, in hologram 57 several interference figures are stored after recording whose respective phase differs by 60°.

After the development of record carrier 57 it is returned in exactly the same position it held upon the recording of the hologram. For reconstructing the hologram in the position of object 53, record carrier 57 is again illuminated with reference wave 501. Since furthermore, as in the recording of the hologram, object 53 is applied with object wave 500, there appear interferences between the reconstructed image of object 53 and object 53 itself. In this reconstruction, the rotation direction of circularly polarized waves 500 and 501 show the same sense (through corresponding orientation of the λ/4 plates in the two beam paths); the individual areas of the holographic recording are then optically equal.

The interference image formed now comprises three components which correspond to the various transmission directions of polarizers 58, and which consequently have different phases. If this interference field is observed with a polarization camera 59 (through record carrier 57), each of the three image converter tubes receives a predetermined share of the three phase-shifted components; by combining these components, the associated phase and consequently the sign of deformation can be determined for each point of the interference field.

This determination of the absolute phase corresponds to the method generally applied to a sinusoidal signal ($Y = M + A \cdot \sin(X + \psi)$) to determine its unknown amplitude A, phase $\psi$, and mean value M by means of three test points having a known mutual phase shift (in the present case ±120°).

FIG. 5B shows an alternative arrangement of the holographic interference, wherein instead of a polarization camera three image converter tubes 505a to 505c without preceding polarization filters are used; the tubes are provided behind the holographic record carrier 57 which in turn is preceded by three polarization filters 504a to 504c spatially associated to the image converter tubes and having transmission directions respectively differing by 60°. The recording of the hologram, and the evaluation of the interference image are effected as in the case of FIG. 5A.

The evaluation of the image recorded by polarization camera 59 (or by the three tubes 505a to 505c respectively) through local analysis of the respective polarization direction is effected in the same manner as in the above described examples: luminance and chrominance signals are again the carriers of the data that will be evaluated.

FIG. 5A also shows a simplified circuit diagram for the generation of signals which functionally correspond to the luminance and chrominance signal. In block 507, the sum of the three output signals of the image converter tubes in polarization camera 59 are generated (corresponding to the luminance). The electronic circuit blocks 508 and 509 generate the linear combinations of the output signals, i.e. $R - \frac{1}{2}(G + B)$ and $B - G$, respectively. These linear combinations substantially correspond to signals I and Q (mentioned earlier) whose superposition with a phase difference of 90° produces the chrominance signal. The amplitude ratio of the output signals of blocks 508 and 509 corresponds to the tangent of the phase angle $\psi$ in the chrominance signal. The phase angle itself can thus be determined from the corresponding inverse trigometric function as the arc tangent value of the amplitude ratio; for that purpose, by means of the amplitudes digitalized in blocks 510a and 510b, a read-only memory (ROM) 511 is addressed containing the value range for the arc tangent function. The determined phase value $\psi$ is applied via a summation circuit 514 to a colour monitor 512, as a hue information together with the luminance signal. If desired, a computer 513 can further be connected to polarization camera 59 and colour monitor 512 for digital processing capability.

The above mentioned linear combination of the individual signals is concluded from the following: the signal produced in a continuous phase shift of the two interfering beams is periodical and sinusoidal:

$$Y = M + A \cdot \sin(X + \psi)$$

Its amplitude A, its mean value M, and its phase $\psi$ are unknown. The three-point scanning of this signal by means of the three differently oriented polarizers provides the following signals:

$$R = M + A \cdot \sin \psi$$

$$B = M + A \cdot \sin (\psi + 120°)$$

$$G = M + A \cdot \sin (\psi - 120°)$$

Taking into consideration the trigonometric relations $$-\sin x = \sin(x - 120°) + \sin(x + 120°)$$

$$\cos x = \sqrt{\frac{1}{3}} \{\sin(x - 120°) - \sin(x + 120°)\}$$

and $$M = \tfrac{1}{3}(R + G + B)$$

$$A \cdot \sin \psi = R - M = \tfrac{1}{3}(2R - B - G)$$

$$A \cdot \sin (\psi + 120°) = B - M$$

$$A \cdot \sin (\psi - 120°) = G - M$$

there applies for the required phase $\psi$:

$$\tan \psi = \sqrt{\frac{2R - (B + G)}{3(G - B)}}$$

From this equation it is apparent that the numerator and denominator, with the exclusion of a constant, represent the output signals of the electronic circuit blocks 508 and 509 which are used for addressing the arc tangent table in read-only memory 511.

While the invention has been particularly shown and described with reference to the preferred embodiments thereof, it will be understood by those skilled in the art that various changes in form and detail may be made therein without departing from the spirit and scope of the invention.

What is claimed is:

1. A method for interferometrically determining the topography of a surface by investigating the polarization state of a light wave field reflected from said surface comprising the steps of:
    illuminating the surface to be investigated with a first circularly polarized light beam to obtain a beam reflected from said surface to be investigated;
    deriving a plane polarized beam from said first circularly polarized beam;
    illuminating a reference surface with said plane polarized beam to obtain a corresponding plane polarized beam reflected from said reference surface;
    converting said beam reflected from the reference surface into a second circularly polarized beam, the direction of polarization of said second circularly polarized beam being opposite to the direction of polarization of said first beam;
    superimposing said two circularly polarized light beams to form a combined light wave field containing, by way of its resultant polarization state, data characterizing the surface topography of the surface to be investigated;
    directing said combined light wave field onto polarization camera means; and
    measuring for each point of the combined light wave field the intensity transmitted by said polarization camera means for three different transmission directions, each differing from the other by 60°.

2. An apparatus for determining the polarization state of a light wave field by evaluating the local polarization ellipse which characterizes each point in said field comprising:
    (a) a polarization TV camera incorporating three image pick-up tubes each having an optical polarizer in optical communication therewith, the light transmission direction of said three polarizers being 0°, 60° and 120°, respectively, means for transmitting an equal intensity of said light wave field to each of said tubes, imaging means for directing the light wave field to said transmitting means, and means for scanning said tubes to obtain therefrom the intensities $I_R$, $I_G$ and $I_B$ of the light wave field corresponding to said three directions, respectively, wherein said intensities are related to the points of intersection R, G, B of said transmission directions with said polarization ellipse by $R = \sqrt{I_R}$, $G = \sqrt{I_G}$ and $B = \sqrt{I_B}$;
    (b) means responsive to said light intensities and said corresponding transmissive directions for generating the polarization state of said wave field from the luminance signal given by $$Y = 0.3R + 0.59G + 0.11B$$

and the chrominance signal given by $$I = 0.6R - 0.28G - 0.32B$$

$$Q = 0.21R - 0.53G + 0.31B; \text{ and}$$

(c) color TV display means for displaying a two-dimensional TV picture of said polarization state as a function of brightness, hue and saturation, said brightness being provided by said luminance signal and said hue and saturation being provided by said chrominance signal.

3. An apparatus for determining the polarization state of a light wave field by evaluating the local polarization ellipse which characterizes each point in said field, said apparatus comprising:
    (a) a polarization TV camera including a single image converter tube having a light admitting surface;
    (b) a polarization filter mounted in front of said image converter tube for optical communication therewith;
    (c) a polarization-rotating layer arranged in front of said filter to be in optical communication with said filter, said layer having zones of three thicknesses for rotating the polarization direction of the light wave field incident thereon by 0°, 60° and 120°, respectively, upon passage through said layer;
    (d) means for scanning said image converter tube to obtain three successive signals corresponding to the light wave field passed through said three zones of the polarization-rotating layer;
    (e) decoder means to electronically separate said successive signals into intensity signals $I_R$, $I_G$ and $I_B$ of the light wave field corresponding to said three polarization directions;
    (f) means responsive to said intensity signals and said corresponding polarization directions for generating the chrominance signal given by $$I = 0.6\sqrt{I_R} - 0.28\sqrt{I_G} - 0.32\sqrt{I_B}$$

$$Q = 0.21\sqrt{I_R} - 0.53\sqrt{I_G} + 0.31\sqrt{I_B}$$

and luminance signal given by $$Y = 0.3\sqrt{I_R} + 0.59\sqrt{I_G} + 0.11\sqrt{I_B}$$

and thereby generating the polarization state of said light wave field; and (g) color TV display means for displaying a two-dimensional TV picture of said polarization state as a function of brightness, hue and saturation, said brightness being provided by said luminance signal and said hue and saturation being provided by said chrominance signal.

4. The apparatus of claim 2 or 3 further comprising: means for illuminating a surface with a polarized incident light beam to provide for a corresponding light wave field reflected from said surface to investigate the topography of said surface by determining the polarization state of said reflected light wave field.

5. The apparatus of claim 2 or 3 further comprising interferometric means for providing said light wave field for determining the polarization state thereof by interference of a first circularly polarized light wave field reflected from an object surface and a second circularly polarized light wave field reflected from a reference surface, said second circularly polarized light wave field being derived from said first light wave field and of opposite polarization direction to said first light wave field.

6. A method of identifying a surface by determining the polarization state of a light wave field radiating therefrom by evaluating the local polarization ellipse which characterizes each point in said field, said method comprising the steps of:

(a) illuminating the surface to be identified with a plane polarized incident light wave field and obtaining an elliptically polarized light wave field upon reflection of said incident light wave field from said surface;

(b) measuring for each point of said elliptically polarized light wave field the intensities $I_R$, $I_G$ and $I_B$ transmitted by polarization TV camera means for three different transmission directions designated as r, g and b, respectively, each of said directions differing from the other by 60° wherein said intensities are related to the points of intersection R, G and B of said transmission directions r, g and b, respectively, with said polarization ellipse by $R = \sqrt{I_R}$, $G = \sqrt{I_G}$ and $B = \sqrt{I_B}$, said camera means including three image converter tubes each having an optical polarizer in optical communication therewith, the light transmission direction of said polarizers differing from each other by 60°, a plurality of beam splitters oriented relative to each of said converter tube-polarizer combinations to transmit equal intensity of the elliptically polarized light wave field to each of said converter tubes and optical imaging means for directing said elliptically polarized light wave field to said beam splitters;

(c) processing said intensities transmitted in said directions to obtain the luminance signal given by $$Y = 0.3R + 0.59G + 0.11B$$

and the chrominance signal given by $$I = 0.6R - 0.028G - 0.32B$$

$$Q = 0.21R - 0.53G + 0.31B$$

and thereby the polarization state corresponding to each point of said light wave field; and (d) displaying on color TV display means the polarization state corresponding to each point of said light wave field in terms of local brightness, hue and saturation said brightness being obtained from said luminance signal and said hue and saturation being obtained from said chrominance signal.

7. A method for determining the polarization state of a light wave field by evaluating the local polarization ellipse which characterizes each point in said field, said method comprising the steps of:

directing a light wave field whose polarization state is to be determined onto polarization TV camera means for measuring the intensities $I_R$, $I_G$ and $I_B$ of said light wave field along three different directions designated as r, g and b, respectively, each of said directions differing from the other by 60° wherein said intensities are related to the points of intersection R, G and B of said polarization ellipse with said directions r, g and b, respectively, by $R = \sqrt{I_R}$, $G = \sqrt{I_G}$ and $B = \sqrt{I_B}$, wherein the camera means including an image converter tube having a light admitting surface optically communicating with a polarization filter in front thereof and an optical polarization-rotating layer in optical communication with said filter, said layer having zones of three thicknesses for rotating the polarization direction of the light wave field incident thereon by 0° (corresponding to direction r), 60° (corresponding to direction g) and 120° (corresponding to direction b), respectively, upon passage through said layer;

simultaneously measuring the intensities $I_R$, $I_G$ and $I_B$ of said light wave having said corresponding differing polarization directions;

processing said intensities to obtain the luminance signal given by $$Y = 0.3R + 0.59G + 0.11B$$

and chrominance signal given by
$$I = 0.6R - 0.028G - 0.32B$$

$$Q = 0.21R - 0.53G - 0.31R$$

and thereby the polarization state of said light wave field; and displaying on two-dimensional color TV display means said polarization state in terms of varying local brightness, hue and saturation, said brightness being determined by said luminance signal and said hue and saturation being determined by said chrominance signal.

* * * * *